United States Patent
Adkins, Jr. et al.

(10) Patent No.: US 10,085,929 B2
(45) Date of Patent: Oct. 2, 2018

(54) COMPOSITIONS, KITS AND METHODS FOR MAINTAINING EYELID HYGIENE

(71) Applicant: OCuSOFT, Inc., Richmond, TX (US)

(72) Inventors: Nat Adkins, Jr., Richmond, TX (US); Cynthia Barratt, Richmond, TX (US)

(73) Assignee: OCuSOFT, Inc., Richmond, TX (US)

( * ) Notice: Subject to any disclaimer, the term of this patent is extended or adjusted under 35 U.S.C. 154(b) by 0 days.

(21) Appl. No.: 15/818,263

(22) Filed: Nov. 20, 2017

(65) Prior Publication Data

US 2018/0071192 A1 Mar. 15, 2018

Related U.S. Application Data

(62) Division of application No. 15/090,386, filed on Apr. 4, 2016, now Pat. No. 9,833,399.

(51) Int. Cl.

| | |
|---|---|
| *A61K 8/68* | (2006.01) |
| *A61K 8/42* | (2006.01) |
| *A61K 8/86* | (2006.01) |
| *A61K 8/60* | (2006.01) |
| *A61K 8/04* | (2006.01) |
| *A61K 33/20* | (2006.01) |
| *A61K 9/00* | (2006.01) |
| *A61K 8/34* | (2006.01) |
| *A61K 8/44* | (2006.01) |
| *A61K 8/55* | (2006.01) |
| *A61K 8/88* | (2006.01) |
| *A61K 8/20* | (2006.01) |
| *A61K 8/49* | (2006.01) |
| *A61K 47/02* | (2006.01) |
| *A61K 47/10* | (2017.01) |
| *A61K 47/14* | (2017.01) |
| *A61Q 19/00* | (2006.01) |
| *A61Q 19/10* | (2006.01) |

(52) U.S. Cl.
CPC ............... *A61K 8/68* (2013.01); *A61K 8/046* (2013.01); *A61K 8/20* (2013.01); *A61K 8/345* (2013.01); *A61K 8/42* (2013.01); *A61K 8/442* (2013.01); *A61K 8/4973* (2013.01); *A61K 8/553* (2013.01); *A61K 8/602* (2013.01); *A61K 8/86* (2013.01); *A61K 8/88* (2013.01); *A61K 9/0048* (2013.01); *A61K 33/20* (2013.01); *A61K 47/02* (2013.01); *A61K 47/10* (2013.01); *A61K 47/14* (2013.01); *A61Q 19/005* (2013.01); *A61Q 19/007* (2013.01); *A61Q 19/10* (2013.01); *A61K 2800/49* (2013.01); *A61K 2800/524* (2013.01); *A61K 2800/87* (2013.01); *A61K 2800/884* (2013.01)

(58) Field of Classification Search
CPC . A61K 8/68; A61K 8/046; A61K 8/20; A61K 8/42; A61K 8/4973; A61K 8/602; A61K 8/86; A61K 9/0048; A61K 33/20; A61K 2800/49; A61K 2800/524; A61K 2800/87; A61K 2800/884; A61Q 19/007; A61Q 19/10

See application file for complete search history.

(56) References Cited

U.S. PATENT DOCUMENTS

| | | | |
|---|---|---|---|
| 6,147,118 A * | 11/2000 | Lambers | A61K 8/41 514/603 |
| 7,951,387 B2 | 5/2011 | Witham et al. | |
| 8,202,853 B2 | 6/2012 | Adkins, Jr. | |
| 2009/0300864 A1 * | 12/2009 | Adkins, Jr. | A61K 8/0208 15/104.93 |
| 2010/0119461 A1 | 5/2010 | Bicard-Benhamou et al. | |
| 2010/0140114 A1 * | 6/2010 | Pruitt | A61K 9/0051 206/5.1 |
| 2012/0128763 A1 * | 5/2012 | Maskin | A61K 35/60 424/450 |
| 2015/0196590 A1 | 7/2015 | Sampson et al. | |

OTHER PUBLICATIONS

Search Report and Written Opinion dated Jul. 7, 2016 for related co-pending App. No. PCT/US16/25908.

USPTO NonFinal Office Action dated Apr. 6, 2017 for co-pending U.S. Appl. No. 15/090,386.

\* cited by examiner

*Primary Examiner* — Michael B. Pallay

(74) *Attorney, Agent, or Firm* — D'Ambrosio & Menon, PLLC; Usha Menon

(57) ABSTRACT

A method for treating an ocular condition involves cleansing an eyelid with a first ophthalmic composition, wherein the first ophthalmic composition consists essentially of water, PEG-80 sorbitan laurate, methyl gluceth-20, PEG-120 methyl glucose dioleate, salicyloyl phytosphingosine, decyl glucoside, 1,2 hexanediol, caprylyl glycol, disodium cocoamphodiacetate, panthenol, polyaminopropyl biguanide, sodium chloride, potassium chloride and calcium chloride followed by applying a therapeutically effective amount of a second ophthalmic composition to a margin of the eyelid, wherein the second ophthalmic composition consists essentially of water and hypochlorous acid.

14 Claims, 1 Drawing Sheet

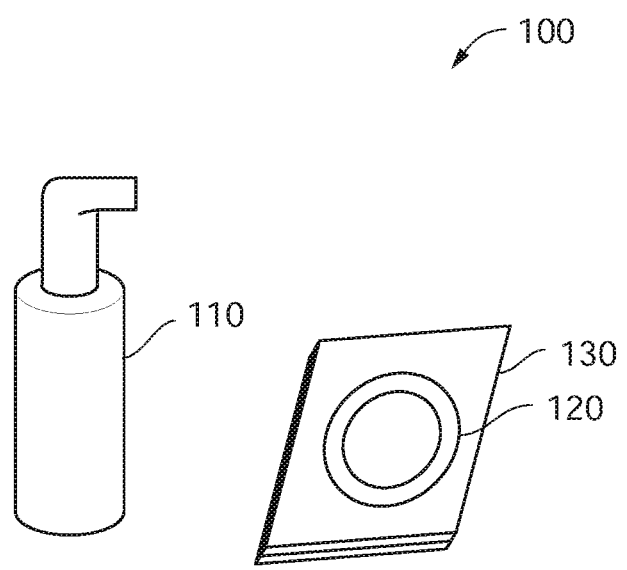

COMPOSITIONS, KITS AND METHODS FOR MAINTAINING EYELID HYGIENE

CROSS REFERENCE TO RELATED APPLICATIONS

This application is a divisional of and claims priority to U.S. Ser. No. 15/090,386 filed on Apr. 4, 2016, the contents of which are incorporated by reference herein.

BACKGROUND

Ocular health refers to eyes as well as structures associated with the eyes, eyelids for example. The eyelids are important in over-all ocular health because they protect the eyes from dangers such as approaching objects or from airborne contaminants, such as pollen, dust particles or other foreign bodies. The eyelids contain essential glands; the lacrimal glands and meibomian glands that produce layers of tear film that are critical for healthy eyes. When an individual blinks, a new tear film is created and tears are distributed across the cornea to lubricate the surface of the eye. This blinking action also "flushes" foreign materials from the eye.

The eyelids, however, are subject to certain problems, which while very common, are none-the-less bothersome, especially for contact lens wearers, and may lead to other more serious complications. One complication is blepharitis. Blepharitis is a common chronic inflammation of the eyelids characterized by a scaly crust on the lid margins. The condition may be caused by a bacterial infection, or it may be allergic in origin or associated with seborrhea of the face and scalp. Treatment usually involves cleansing the eyelids on a regular basis to remove excess oil, debris, and desquamated skin that may be problematic.

Often associated with or secondary to blepharitis is a bacterial infection of the surface of the skin at the edge of the lid know as an internal hordeolum. Other such infections include external hordeolum, commonly referred to styes, which are infections of the tiny oil secreting meibomian glands along the edge of the eyelid, surrounding the eyelashes. A stye begins as a red, tender bump and usually fully develops within three days. Such conditions are accompanied by pain, redness and tenderness of the eyelid (or lid) margins. Although styes are often recurring, regular cleansing of the eyelid margins can minimize such conditions. A second problem is a chalazion, which is an inflammation of the meibomian glands inside the eyelid. Chalazia typically grow slowly over 2-3 weeks and although they do not typically cause pain, they often require surgical intervention if left untreated.

With any of the above-described problems, as well as other medical complications, such as rosacea and seborrhea, proper eyelid hygiene with the use of an eyelid cleanser may minimize the severity of the outbreak, or prevent the problem altogether if caught early. Eyelid cleansers are also used for cleaning eyelashes, eyelids or the periocular area and may be used as a pre-operative scrub to help reduce the presence of harmful bacteria which may cause infection, inflammation, or even endophthalmitis in patients.

SUMMARY

The present application is directed to a first ophthalmic composition comprising: a preservative blend, the preservative blend consisting essentially of a mixture of polyaminopropyl biguanide, a 1,2-glycol and a sphingoid lipid; a surfactant solution; and a moisturizer. The 1,2-glycol may be selected from the group consisting of 1,2-hexanediol, caprylyl glycol, pentylene glycol and mixtures thereof. The sphingoid lipid comprises salicyloyl phytosphingosine. In one aspect, the salicyloyl phytosphingosine is present in a concentration ranging from 0.01 to 1 weight % based on the total weight of the composition.

The surfactant solution comprises an aqueous mixture of a nonionic surfactant and at least one of an amphoteric or an anionic surfactant. The surfactant solution consists essentially of water, sodium chloride, potassium chloride, calcium chloride, disodium cocoamphodiacetate, PEG-80 sorbitan laurate and decyl glucoside. The moisturizer is selected from the group consisting of methyl gluceth-20, sorbital, glycerine, propylene glycol, panthenol, D-panthenol, and D, L-panthenol and mixtures thereof.

The first ophthalmic composition comprises a foam. In one embodiment, the first ophthalmic composition may be dispensed as a pre-lathered foam. The first ophthalmic composition further comprises a foam stabilizer, such as, PEG-120 methyl glucose dioleate.

In one specific embodiment, the first ophthalmic composition consists essentially of water, PEG-80 sorbitan laurate, methyl gluceth-20, PEG-120 methyl glucose dioleate, salicyloyl phytosphingosine, decyl glucoside, 1,2 hexanediol, caprylyl glycol, disodium cocoamphodiacetate, panthenol, polyaminopropyl biguanide, sodium chloride, potassium chloride and calcium chloride.

In another embodiment, the present application is directed to a method for maintaining eyelid hygiene. The method involves cleansing an eyelid with the first ophthalmic composition; and leaving the first ophthalmic composition on the eyelid without rinsing.

In yet another embodiment, the present application is directed to a method for treating an ocular condition. The ocular condition may include blepharitis, Demodex or other bacterial infections, inflammation or even a wound or injury to the eyelid. The method for treatment comprises: cleansing the eyelid with the first ophthalmic composition; and leaving the first ophthalmic composition on the eyelid without rinsing. The method further comprises applying a therapeutically effective amount of a second ophthalmic composition to a margin of the eyelid. The second ophthalmic composition consists essentially of water and hypochlorous acid. In a specific embodiment, the second ophthalmic composition consists essentially of ≥99% weight water and ≤0.02% weight hypochlorous acid. The second ophthalmic composition may be an aqueous gel or spray. This combination therapy involving the first and second ophthalmic composition can expedite wound healing of the eyelids while addressing inflammation and long term eyelid hygiene.

In yet another embodiment, a kit for maintaining eyelid hygiene consists essentially of: a first ophthalmic composition, wherein the first ophthalmic composition consists essentially of water, PEG-80 sorbitan laurate, methyl gluceth-20, PEG-120 methyl glucose dioleate, salicyloyl phytosphingosine, decyl glucoside, 1,2 hexanediol, caprylyl glycol, disodium cocoamphodiacetate, panthenol, polyaminopropyl biguanide, sodium chloride, potassium chloride and calcium chloride; a pharmaceutically acceptable container for containing and dispensing the first ophthalmic composition; and an applicator for applying the first ophthalmic composition to an eyelid. The first ophthalmic composition may have a volume of 25 ml to 100 ml. In a specific aspect, the first ophthalmic composition may have a volume of 50 ml. In one aspect, the applicator comprises a plurality of fabric pads. In a specific aspect, the kit consists essentially of a 50 ml bottle of the first composition and 100 dry lint-free fabric pads.

BRIEF DESCRIPTION OF THE DRAWINGS

FIG. 1 illustrates a kit according to an embodiment of the invention.

DETAILED DESCRIPTION

While the specification concludes with the claims particularly pointing and distinctly claiming the invention, it is believed that the present invention will be better understood from the following description. All percentages and ratios used herein are by weight of the total composition. The present invention can comprise or consist essentially of the components of the present invention as well as other ingredients or elements described herein. As used herein, "comprising" means the elements recited, or their equivalent, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

As used herein, the term "effective amount" of a composition refers to an amount sufficient to elicit the desired biological response. In some embodiments, a therapeutically effective amount of a composition is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition.

According to an embodiment, a first ophthalmic composition is configured for a daily eyelid hygiene management regime. Accordingly, the first ophthalmic composition is formulated as a non-irritating leave-on eyelid cleanser. The first ophthalmic composition includes both anti-bacterial and anti-inflammatory properties. It can also aid in wound-healing of the eyelids. The first ophthalmic composition is suitable for topical application. Topical application is understood to comprise cosmetic and/or dermatological application on the eyelids. The formulation can be used to not only treat the source of most eyelid conditions, but also the resulting symptoms leading to improved patient compliance. The first ophthalmic composition is formulated to effectively eradicate multiple different strains of bacteria commonly found on the eyelids. For example, the first ophthalmic composition can eradicate at least seven different strains of bacteria including methicillin resistant *Staphylococcus aureus* (MRSA) and *Staphylococcus epidermidis* (Staph epi). The first ophthalmic composition is formulated to therapeutically relieve irritation by removing oil, debris, pollen and other contaminants. It also has added anti-inflammatory properties for long term relief from symptoms.

In one embodiment, the first ophthalmic composition comprises a mixture of a preservative blend, a surfactant solution and a moisturizer. The preservative blend comprises a mixture of antimicrobial agents and 1,2-glycol compounds. The antimicrobial agents can treat microorganisms such as bacteria, yeasts and fungi. In one aspect, the antimicrobial agents consist of polyaminopropyl biguanide and a sphingoid lipid.

For the purposes of this invention, polyaminopropyl biguanide is pseudonymous for polyhexamethylene biguanide and polyhexamethylene biguanide hydrochloride. The sphingoid lipid comprises an anti-inflammatory and anti-irritant agent, such as, phytosphingosine (PSG) or a derivative thereof. The term "anti-irritant", as used herein, is an agent that prevents or reduces soreness, roughness, or inflammation of a bodily part, such as, the eyelids. In a specific aspect, the first ophthalmic composition includes PSG which is esterified with salicylic acid. PSG is a natural chemical that is a part of the lipid family. PSG is a water-binding agent that mimics the natural lipid layer of the outer epidermis for increased moisturizing throughout the day. PSG has anti-redness and skin firming properties and can inhibit microorganisms. Beneficially, PSG has both anti-bacterial and wound-healing properties and it acts as an anti-inflammatory at concentrations as low as 0.1%. In one aspect, the first ophthalmic composition comprises salicyloyl PSG between 0.05%-1% by weight and preferably, 0.2% salicyloyl PSG, in each case with respect to the total formulation. The 1,2-glycol compounds can include 1,2-hexanediol, caprylyl glycol and pentylene glycol. Caprylyl glycol is also known as 1,2-octanediol.

The surfactant solution comprising an aqueous mixture of a combination of nonionic surfactants and at least one of amphoteric or anionic surfactants. Suitable amphoteric surfactants include, but are not limited to alkyldimethyl betaines, alkylamido betaines, sulfobetaines, and imidazoline amphoterics. Suitable anionic surfactants include, but are not limited to fatty alcohol sulfates, alpha olefin sulfonates, sulfosuccinates, sarcosinates, phosphate esters, and carboxylates. Suitable nonionic surfactants include, but are not limited to alkanolamids, ethoxylate amids, esters, alkoxylated alcohols, alkylpolyglucosides, amine oxides, sorbitan esters, and ethoxylates.

Polyaminopropyl biguanide is most effective as an antimicrobial agent in pH ranges between 5.5 and 7.5. Therefore, it is desirable to control the pH level of the first ophthalmic composition within this range by use of a blend of surfactants. It is also desirable that the first ophthalmic composition has a foaming ability to facilitate physical cleansing of the eyelid. Consequently, surfactants must be chosen which will both control the pH of the first ophthalmic composition within polyaminopropyl biguanide's effective range and provide the foaming ability necessary to physically clean the eyelid.

Advantageously, the first ophthalmic composition does not include traditional pH adjusters which can be irritating to the eye. In general, surfactants are less irritating to the eye than traditional pH adjusters. Examples of traditional pH adjusters, include basic pH adjusters, such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine), and acidic pH adjusters, such as mineral acids and polycarboxylic acids (e.g., hydrochloric acid, nitric acid, phosphoric acid, sulfuric acid, citric acid, glycolic acid, and lactic acid).

In one embodiment, the surfactant solution comprises disodium cocoamphodiacetate, PEG-80 sorbitan laurate and decyl glucoside. Disodium cocoamphodiacetate is an amphoteric surfactant. PEG-80 sorbitan laurate and decyl glucoside are both nonionic surfactants. Surfactants can reduce irritation and can increase the cleansing ability of the first ophthalmic composition and provide it with a foaming capability. Foams are considered to have optimal cleansing and preventive capability.

The combination of surfactants is added to a modified Ringer's solution. For the purposes of this invention, a modified Ringer's solution is an isotonic aqueous solution of electrolytes which is physiologically compatible with human tissue. In one embodiment, the modified Ringer's solution comprises sodium chloride, potassium chloride, calcium chloride, and water. Modified Ringer's solution is included in the surfactant solution to ensure that the composition will not remove water from the eyelids by osmosis. The modified Ringer's solution comprises sodium chloride, potassium chloride, calcium chloride, and water. Preferably, the water used is purified water. The modified Ringer's solution may also comprise 0.05 to 1.2 wt. % sodium chloride, 0.005 to 0.5 wt. % potassium chloride, 0.005 to 0.5 wt. % calcium chloride, and water. In still another embodiment, the modified Ringer's solution comprises about 0.7 wt. % sodium chloride, about 0.03 wt. % potassium chloride, about 0.033 wt. % calcium chloride, and purified water.

Moisturizers are chemicals that prevent transepidermal water loss and restore moisture to the skin. Moisturizers may prevent water loss by forming a film over the skin to prevent water from evaporating from the skin. Alternatively, moisturizers comprise hydroscopic molecules that draw water from the air into the skin. In one embodiment, the first ophthalmic composition includes a suitable moisturizer such as, but not limited to, methyl gluceth-20, sorbital, glycerine, propylene glycol, carboxylates, amino acids, glucoside derivatives, urea, lactates, and derivatives of pantothenic acid. Examples of derivatives of pantothenic acid include panthenol, D-panthenol, and D, L-panthenol.

In an embodiment, the first ophthalmic composition also comprises a foam stabilizer. A foam stabilizer is a chemical which increases the lifetime of the foam. The foam stabilizer can be a polyethylene glycol diester of methyl glucose and a fatty acid. Suitable fatty acids include oleic acid, steric acid, lauric acid, caprylic acid, and capric acid. Suitably, the foam stabilizer is PEG-120 methyl glucose dioleate.

A specific embodiment of the first ophthalmic composition consists essentially of water, PEG-80 sorbitan laurate, methyl gluceth-20, PEG-120 methyl glucose dioleate, salicyloyl phytosphingosine, decyl glucoside, 1,2 hexanediol, caprylyl glycol, disodium cocoamphodiacetate, panthenol, polyaminopropyl biguanide, sodium chloride, potassium chloride and calcium chloride. The ingredients selected in this embodiment specifically ensure that the formulation possesses anti-bacterial, anti-inflammatory and wound-healing capabilities.

The first ophthalmic composition is effective as a scrub, as it has an antimicrobial effect, but is still practically non-irritating to the eye. The first ophthalmic formulation has these beneficial characteristics because of the combination of polyaminopropyl biguanide, 1,2-glycol compounds and the sphingoid lipid. Advantageously, the formulation does not contain astringents such as, zinc or zinc salts. Examples of zinc salts include zinc acetate, zinc lactate, zinc gluconate, zinc citrate, zinc butyrate, and zinc sterate.

According to an embodiment, a method of cleansing the eyelid comprises providing the first ophthalmic composition disclosed herein. The method further involves cleansing the eyelids with an effective amount of the formulation. The first ophthalmic composition can be allowed to remain on the eyelid after cleansing without rinsing. This is because the first ophthalmic composition is formulated to be mild enough to be left on the eyelid. The ability of the first ophthalmic composition to be left on the eyelid rather than rinsed off increases the formulation's anti-microbial effect. In general, the longer an anti-microbial composition like the first eyelid composition is allowed to contact the pathogens, the more pathogens it will kill.

In another aspect of the method of cleansing the eyelid, the first ophthalmic composition is applied to the eyelid from an applicator. The applicator may be a dry and substantially lint-free fabric pad, such as, a rayon pad or a rayon and polypropylene fabric blend. The fabric pad can comprise a textured surface. The first ophthalmic composition may be rubbed on the eyelid with the fabric pad to induce foaming, which assists in the cleansing ability of the formulation. In one embodiment, the first ophthalmic composition may be combined with the fabric pad to form an apparatus for cleansing the eyelids. In yet another embodiment, an eyelid cleansing apparatus comprises a fabric pad that is pre-moistened with the first ophthalmic composition.

In another embodiment, as shown in FIG. 1, an eyelid cleansing kit 100 comprises a pharmaceutically acceptable container/dispensing device 110. A predetermined amount of the first ophthalmic composition is contained inside the container 110. The kit further comprises an applicator 120.

The container 110 may be a pump dispenser known in the art. The container 110 can be configured to deliver the first ophthalmic composition as pre-lathered foam without requiring any outside physical or mechanical action to prevent loss of the composition. For convenience and economy, the container 110 may be configured to contain about 25 ml to 100 ml of the first ophthalmic composition. Preferably, the container 110 may be configured to contain about 50 ml of the first ophthalmic composition.

The applicator 120 is configured for receiving the first ophthalmic composition. In one aspect, the applicator 120 includes one or more absorbent pads. The pads 120 comprise a lint-free fabric, such as, rayon or another suitable material that can receive the first ophthalmic composition. The pads 120 may be single use disposable pads. The eyelid cleansing kit 100 can include between 1-100 pads 120. In one embodiment, one or more of the pads 120 may be contained within a sealable container 130. In one aspect, the sealable container 130 may comprise a box or a package. The package may be made of any suitable material including plastic or metal foil material. The pump dispenser 110 may also be enclosed in suitable housing (not shown). In another aspect, the applicator 120 includes one or more swabs or swab sticks (not shown). In another aspect of the invention, paper towels, cotton balls or even the fingertips can be employed to apply the first ophthalmic composition to the eyelid.

In another embodiment, the kit consists essentially of a plurality of fabric pads pre-moistened with the first ophthalmic composition. The pre-moistened fabric pads may be individually packaged for use.

Blepharitis is a common eye disorder characterized by an inflammation of the eyelids that causes red, irritated, itchy eyelids and the formation of dandruff-like scales on eyelashes. Blepharitis may be caused by bacteria or skin conditions, such as, dandruff of the scalp or acne rosacea. Anterior blepharitis occurs at the outside front edge of the eyelid where the eyelashes are attached. The root cause of anterior blepharitis is the overproduction of oils. The first ophthalmic formulation is effective for daily use in all blepharitis conditions. However, in the most severe conditions, it may be used in combination with a second ophthalmic formulation containing hypochlorous acid to optimally treat severe cases of anterior blepharitis.

According an embodiment, a method of treating an ocular condition (such as, blepharitis, Demodex infestations, or other infections) includes cleansing the eyelids with an effective amount of the first ophthalmic composition. This is followed by applying an effective amount of a second ophthalmic composition. The second ophthalmic composition may be applied to the eyelid margin with clean fingers or using a suitable applicator. The second ophthalmic composition may also be allowed to left on without rinsing. According to an embodiment, the second ophthalmic composition is an aqueous gel or spray. The second ophthalmic composition consists essentially of ≥99% water and ≤0.02% hypochlorous acid. The second ophthalmic formulation may be devoid of a surfactant.

Since the second ophthalmic composition contains hypochlorous acid but not a surfactant, it may not optimally dissolve and remove oil, debris and desquamated skin. Therefore, a combination therapy involving the first and second ophthalmic compositions may be effective in debriding the oil, scales and debris often associated with eyelid irritations. This combination therapy is fast acting against microorganisms and expedites wound healing of the eyelids while addressing inflammation and long term eyelid hygiene.

In another embodiment, a kit of treating an ocular condition consists essentially of: 1) a pharmaceutically acceptable first container for containing and dispensing the first ophthalmic composition as a pre-lathered foam; and 2) a second pharmaceutically acceptable containing for containing and dispensing the second ophthalmic composition in either a gel or spray form. In yet another embodiment, a kit for treating an ocular condition consists essentially of: 1) a pharmaceutically acceptable first container for containing and dispensing the first ophthalmic composition as a pre-lathered foam; 2) a second pharmaceutically acceptable container for containing and dispensing the second ophthalmic composition as a gel; and 3) a third pharmaceutically acceptable container for containing and dispensing the second ophthalmic composition as a spray. Each of the kits may further include a plurality of the dry fabric pads described earlier for receiving an effective amount of the first and/or second ophthalmic composition.

Test Results

The first ophthalmic composition of the present invention has an anti-microbial effect with a lower level on irritation than other antimicrobial compositions. To confirm the characteristic of the composition of this invention both the irritation and antimicrobial effects of the composition were tested. The test material was instilled into one eye of each of nine albino rabbits, 3 eyes were unrinsed, 3 eyes were rinsed 3 to 4 seconds after exposure and 3 eyes were rinsed following a 30 second contact period. Instillation of sample into the eyes of rabbits with no rinse elicited minimal ocular irritation. The maximum mean irritation score was 3.33/110.0 at the 1 hour observation, all irritation cleared by the 48 hour observation. Instillation sample into the eyes of rabbits with 4 second rinse elicited minimal ocular irritation. The maximum mean irritation score was 4.0/110.0 at the 1 hour observation, all irritation cleared by the 48 hour observation. Instillation of sample into the eyes of rabbits with a 30 second rinse elicited minimal ocular irritation. The maximum mean irritation score was 4.01/110.0 at the 1 hour observation, all irritation cleared by the 48 hour observation. Based upon the results of the study this material would not be considered an eye irritant in either unrinsed or rinsed eyes.

Another study used an In-Vitro Time-Kill Method to evaluate the antimicrobial properties of the first ophthalmic composition containing 0.2% salicyloyl PSG and a second ophthalmic composition (in both gel and spray form) containing 0.02% hypochlorous acid when challenged with suspensions of seven bacterial species. This procedure was based upon the methodology described in ASTM E2783-11, *Standard Test Method for Assessment of Antimicrobial Activity for Water Miscible Compounds Using a Time-Kill Procedure*. All testing was performed in accordance with Good Laboratory Practices, as specified in 21 CFR Part 58. It was found that the first ophthalmic composition reduced the microbial populations of *Escherichia coli, Moraxella catarrhalis, Serratia marcescens,* and *Staphylococcus epidermidis* by greater than 6.0 Log 10 following the 60 minute and 120 minute exposures. The microbial populations of *Pseudomonas aeruginosa, Staphylococcus aureus,* and *Staphylococcus aureus* MRSA were reduced by greater than 2.0 Log 10 following 60 minute exposures and were reduced by greater than 3.0 Log 10 following 120 minute exposures to the first ophthalmic composition. Further, it was found that the second ophthalmic composition reduced the microbial populations of all these microorganisms by greater than 4.9 Log 10 following the 1 minute product exposure including the 1 minute time exposure after 7 days, 14 days, 21 days, and 30 days. The reduction was maintained or increased after 60 and 120 minutes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

The invention claimed is:

1. A method for maintaining eyelid hygiene comprising:
   cleansing an eyelid with an effective amount of a first ophthalmic composition; and
   leaving the first ophthalmic composition on the eyelid without rinsing,
      wherein the first ophthalmic composition comprises:
         a preservative blend, the preservative blend consisting essentially of a mixture of polyaminopropyl biguanide, a 1,2-glycol and a sphingoid lipid, the sphingoid lipid comprises salicyloyl phytosphingosine;
         a surfactant solution; and
         a moisturizer.

2. The method according to claim 1, wherein the 1,2-glycol is selected from the group consisting of 1,2-hexanediol, caprylyl glycol, pentylene glycol and mixtures thereof.

3. The method according to claim 1, wherein the salicyloyl phytosphingosine is present in a concentration ranging from 0.01 to 1 weight % based on the total weight of the composition.

4. The method according to claim 1, wherein the surfactant solution comprises an aqueous mixture of a nonionic surfactant and at least one of an amphoteric or an anionic surfactant.

5. The method according to claim 4, wherein the surfactant solution consists essentially of water, sodium chloride, potassium chloride, calcium chloride, disodium cocoamphodiacetate, PEG-80 sorbitan laurate and decyl glucoside.

6. The method according to claim 1, wherein the moisturizer is selected from the group consisting of methyl gluceth-20, sorbital, glycerine, propylene glycol, panthenol, D-panthenol, and D, L-panthenol and mixtures thereof.

7. The method according to claim 1, wherein the first composition further comprises a foam stabilizer.

8. The method according to claim 7, wherein the foam stabilizer comprises PEG-120 methyl glucose dioleate.

9. The method according to claim 1, wherein the first ophthalmic composition is a foam.

10. A method for treating an ocular condition comprising:
cleansing an eyelid with an effective amount of a first ophthalmic composition; and
leaving the first ophthalmic composition on the eyelid without rinsing,
wherein the first ophthalmic composition comprises:
water, PEG-80 sorbitan laurate, methyl gluceth-20, PEG-120 methyl glucose dioleate, salicyloyl phytosphingosine, decyl glucoside, 1,2 hexanediol, caprylyl glycol, disodium cocoamphodiacetate, panthenol, polyaminopropyl biguanide, sodium chloride, potassium chloride and calcium chloride.

11. The method according to claim 10, further comprising applying a therapeutically effective amount of a second ophthalmic composition to a margin of the eyelid.

12. The method according to claim 11, wherein the second ophthalmic composition consists essentially of water and hypochlorous acid.

13. The method according to claim 12, wherein the second ophthalmic composition consists essentially of ≥99% water and ≤0.02% hypochlorous acid.

14. The method according to claim 11, wherein the second ophthalmic composition is an aqueous gel or spray.

* * * * *